United States Patent [19]

Maurer et al.

[11] Patent Number: 4,513,000
[45] Date of Patent: Apr. 23, 1985

[54] INSECTICIDAL N-SUBSTITUTED O-PYRAZOL-4-YL CARBAMATES AND USE THEREOF

[75] Inventors: Fritz Maurer, Wuppertal; Bernhard Homeyer, Leverkusen; Ingeborg Hammann, Cologne, all of Fed. Rep. of Germany

[73] Assignee: Bayer Aktiengesellschaft, Leverkusen, Fed. Rep. of Germany

[21] Appl. No.: 433,337

[22] Filed: Oct. 8, 1982

[30] Foreign Application Priority Data

Oct. 29, 1981 [DE] Fed. Rep. of Germany ....... 3142857

[51] Int. Cl.³ ................ A01N 43/56; C07D 231/14; C07D 403/12
[52] U.S. Cl. .................................. 514/407; 548/374; 548/377
[58] Field of Search ............ 548/373, 374, 375, 376, 548/377, 378; 424/285, 273 P; 560/137

[56] References Cited

U.S. PATENT DOCUMENTS 3,857,860 12/1974 Kuhle et al. ..................... 560/137
4,181,734 1/1980 D'Silva .......................... 424/285
4,418,073 11/1983 Maurer et al. ................. 424/273 P

FOREIGN PATENT DOCUMENTS 3023675 6/1980 Fed. Rep. of Germany ... 424/273 P
0043917 1/1982 Fed. Rep. of Germany ... 424/273 P
282655 8/1952 Switzerland .................. 424/273 P

*Primary Examiner*—Henry R. Jiles
*Assistant Examiner*—J. G. Mullins
*Attorney, Agent, or Firm*—Sprung Horn Kramer & Woods

[57] ABSTRACT

N-substituted O-pyrazol-4-yl carbamates of the general formula

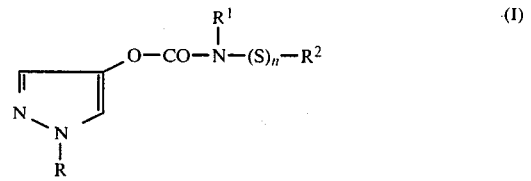

are new and are obtained when
(a) a 4-hydroxy-pyrazole of the general formula

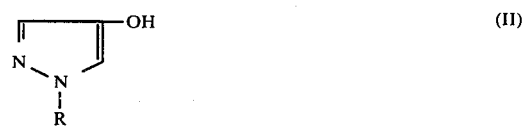

is reacted with an N-sulphenylated carbamoyl halide of the formula

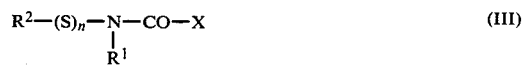

or
(b) a 4-hydroxy-pyrazole of formula (II) is reacted with an acylating agent of the general formula

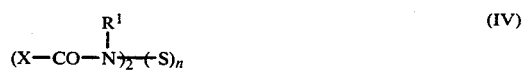

or
(c) an O-pyrazol-4-yl carbamate of the general formula

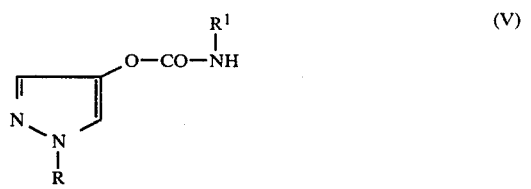

is reacted with a sulphenyl halide of the general formula

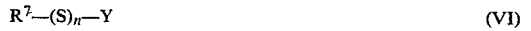

The new N-substituted O-pyrazol-4-yl carbamates of the formula (I) are distinguished by high activity as pest-combating agents, in particular by high insecticidal and nematicidal activity.

7 Claims, No Drawings

INSECTICIDAL N-SUBSTITUTED O-PYRAZOL-4-YL CARBAMATES AND USE THEREOF

The present invention relates to certain new N-substituted O-pyrazol-4-yl carbamates, to processes for their production, and to their use as pest-combating agents, especially as insecticides, acaricides and nematicides.

It is known that certain N,N-dimethyl O-pyrazolyl carbamates, such as N,N-dimethyl O-(1-phenyl-3-methylpyrazol-5-yl)carbamate and N,N-dimethyl O-(1-isopropyl-3-methyl-pyrazol-5-yl)carbamate, possess insecticidal properties (see Swiss Patent Specification 282,655.)

However, the insecticidal action of these compounds is not always satisfactory, particularly in the case of low active compound concentrations and use amounts.

The present invention now provides, as new compounds, the N-substituted O-pyrazol-4-yl carbamates of the general formula

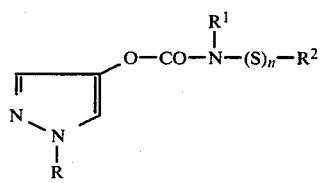

in which
R represents an optionally substituted alkyl, alkenyl, alkinyl, aralkyl or cycloalkyl radical,
$R^1$ represents an optionally substituted alkyl radical having more than one carbon atom, an alkenyl radical, an alkinyl radical or a cycloalkyl radical,
n is 1 or 2, and
$R^2$ represents an optionally substituted alkyl, alkenyl, alkinyl, cycloalkyl or aryl radical, or represents the radical

wherein
$R^3$ represents an alkyl, alkenyl, alkinyl or cycloalkyl radical, and
$R^4$ represents an alkyl, alkenyl, alkinyl, cycloalkyl, aryl, aralkyl, alkoxycarbonyl, alkenoxycarbonyl, alkinoxycarbonyl, aryloxycarbonyl, alkyl-aryloxycarbonyl, alkoxyaryloxycarbonyl, alkylthiocarbonyl, arylthiocarbonyl, alkyl-amino-carbonyl, dialkyl-amino-carbonyl, aminocarbonyl, halogenocarbonyl, alkyl-pyrazol-4-oxy-carbonyl, alkenyl-pyrazol-4-oxy-carbonyl, alkinyl-pyrazol-4-oxy-carbonyl, cycloalkylpyrazol-4-oxy-carbonyl or 2,3-dihydro-2,2-dimethyl-7-benzofuranyl-oxycarbonyl radical, or represents the radical

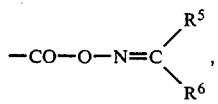

wherein
$R^5$ represents a hydrogen atom, an alkyl radical or a mono- or di-alkylamino-carbonyl radical, and
$R^6$ represents an alkyl, alkylthio, cyano-alkylthio, alkyl-sulphonyl-alkyl or alkylthioalkyl radical, or
$R^5$ and $R^6$ together represent an alkanediyl radical which is optionally interrupted by oxygen, sulphur, or a sulphinyl or sulphonyl grouping,
or wherein
$R^3$ and $R^4$ together represent a saturated or unsaturated hydrocarbon chain which is optionally interrupted by nitrogen, oxygen or sulphur.

According to the present invention we further provide a process for the production of a compound of the present invention characterized in that
(a) a 4-hydroxy-pyrazole of the general formula

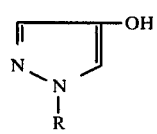

in which
R has the meaning given above,
is reacted with an N-sulphenylated carbamoyl halide of the general formula

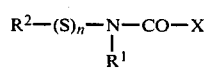

in which
$R^1$, $R^2$ and n have the meanings given above, and
X represents a fluorine or chlorine atom,
if appropriate in the presence of an acid acceptor and, if appropriate, using a diluent; or
(b) a 4-hydroxy-pyrazole of formula (II), as defined in reaction variant (a), is reacted with an acylating agent of the general formula

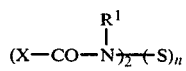

in which
X, $R^1$ and n have the meanings given above,
if appropriate in the presence of an acid acceptor and, if appropriate, using a diluent and, if appropriate, in the presence of a further compound which can be carbamoylated; or
(c) an O-pyrazol-4-yl carbamate of the general formula

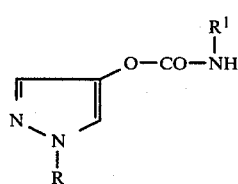

in which
R and $R^1$ have the meanings given above,
is reacted with a sulphenyl halide of the general formula

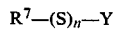

in which
R⁷ represents a halogen atom, or has any of the meanings given above for R²,
n has the meaning given above, and
Y represents a fluorine, chlorine or bromine atom,
if appropriate in the presence of an acid acceptor and, if appropriate, in the presence of a diluent, and in the case in which R⁷ represents a halogen atom, in the presence of a further carbamate of the formula (V).

The new N-substituted O-pyrazol-4-yl carbamtes according to the present invention of the formula (I) are distinguished by high activity as pest-combating agents, in particular by high insecticidal and nematicidal activity.

Surprisingly, the compounds according to the invention, of the formula (I), exhibit a substantially higher insecticidal and nematicidal action than known compounds of similar constitution and identical direction of action, such as the N,N-dimethyl O-pyrazolyl carbamates already mentioned: N,N-dimethyl O-(1-phenyl-3-methylpyrazol-5-yl)carbamate and N,N-dimethyl O-(1-isopropyl-3-methyl-pyrazol-5-yl)carbamate.

Preferred N-substituted O-pyrazol-4-yl carbamates according to the present invention are those in which
R represents a straight-chain or branched alkyl radical which has 1 to 6 carbon atoms and is optionally substituted by halogen (such as fluorine and/or chlorine), cyano, or alkoxy or alkylthio, each having 1 to 4 carbon atoms in the alkyl part; represents an alkenyl or alkinyl radical, each having 3 to 5 carbon atoms; represents a cycloalkyl radical having 3 to 7 carbon atoms or represents an aralkyl radical having 1 to 4 carbon atoms in the alkyl part and 6 to 10 carbon atoms in the aryl part;
R¹ represents straight-chain or branched alkyl radical having 2 to 6 carbon atoms, an alkenyl or alkinyl radical, each having 3 to 5 carbon atoms, or a cycloalkyl radical, having 3 to 7 carbon atoms; n is 1 or 2;
R² represents an alkyl radical which has 1 to 6 carbon atoms and is optionally substituted by halogen, (such as, especially, fluorine and/or chlorine); represents an alkenyl or alkinyl radical having 3 to 5 carbon atoms; represents a cycloalkyl radical having 3 to 7 carbon atoms or a phenyl radical which is optionally mono-substituted or polysubstituted by halogen, cyano, nitro, or optionally halogen-substituted alkyl and alkoxy having 1 to 4 carbon atoms; or represents the radical

wherein
R³ represents a straight-chain or branched alkyl radical having 1 to 6 carbon atoms, an alkenyl or alkinyl radical having 3 to 5 carbon atoms, or a cycloalkyl radical having 3 to 7 carbon atoms, and
R⁴ represents a straight-chain or branched alkyl radical having 1 to 6 carbon atoms, an alkenyl or alkinyl radical having 3 to 5 carbon atoms, a cycloalkyl radical having 3 to 7 carbon atoms, an aryl radical having 6 to 10 carbon atoms, an aralkyl radical having 6 to 10 carbon atoms in the aryl part and 1 to 4 carbon atoms in the alkyl part, an alkoxycarbonyl radical having 1 to 4 carbon atoms in the alkyl part, an alkene-oxycarbonyl or alkine-oxycarbonyl radical, each having 3 to 5 carbon atoms in the alkenyl or alkinyl part, an aryloxycarbonyl radical having 6 to 10 carbon atoms in the aryl part, an alkyl-aryloxy-carbonyl or alkoxy-aryloxycarbonyl radical having 1 to 4 carbon atoms in the alkyl part and 6 to 10 carbon atoms in the aryl part, an alkylthiocarbonyl radical having 1 to 6 carbon atoms in the alkyl part, an arylthiocarbonyl radical having 6 to 10 carbon atoms in the aryl part, an alkyl-aminocarbonyl or dialkyl-aminocarbonyl radical, each having 1 to 6 carbon atoms in the alkyl part, an aminocarbonyl radical, a halogenocarbonyl radical (fluorine, chlorine or bromine being preferred halogens), an alkyl-pyrazol-4-oxycarbonyl radical having 1 to 6 carbon atoms in the alkyl part, an alkenyl-pyrazol-4-oxy-carbonyl or alkinyl-pyrazol-4-oxy-carbonyl radical, each having 3 to 5 carbon atoms in the alkenyl or alkinyl part, cycloalkyl-pyrazol-4-oxy-carbonyl radical, having 3 to 7 carbon atoms in the cycloalkyl part, 2,3-dihydro-2,2-dimethyl-7-benzofuranyl-oxycarbonyl radical or the radical

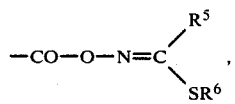

in which
R⁵ represents a hydrogen atom, an alkyl mono- or dialkylaminocarbonyl radical, each having 1 to 4 carbon atoms in the alkyl part, and
R⁶ represents an alkyl, alkylthio, cyano-alkylthio, alkylsulphonylalkyl or alkylthio-alkyl radical, each having 1 to 4 carbon atoms in the alkyl part, or
R⁵ and R⁶ together represent an alkanediyl radical which has 2 to 8 carbon atoms and is optionally interrupted by oxygen, sulphur or a sulphinyl or sulphonyl grouping,
or wherein
R³ and R⁴ together represent a saturated or unsaturated hydrocarbon chain which has 3 to 8 carbon atoms and is optionally interrupted by nitrogen, oxygen or sulphur. Very particularly preferred compounds of the present invention are those in which
R represents a methyl, ethyl, n-propyl, iso-propyl, n-butyl, iso-butyl, sec.-butyl, tert.-butyl, 2-methyl-but-2-yl, 2,2-dimethylprop-1-yl, allyl, propargyl, cyclopropyl, cyclobutyl, cyclopentyl or cyclohexyl radical,
R¹ represents an ethyl, n-propyl, iso-propyl, n-butyl, iso-butyl, sec.-butyl, tert.-butyl, allyl, propargyl, cyclopropyl, cyclobutyl or cyclopentyl radical,
n is 1 or 2,
R² represents a methyl, ethyl, n-propyl, iso-propyl, n-butyl, iso-butyl, sec.-butyl, tert.-butyl, 2-methyl-but-2-yl, 2,2-dimethylprop-1-yl, trichloromethyl, dichloro-fluoromethyl, chloro-difluoromethyl, trifluoromethyl, allyl, propargyl, cyclopropyl, cyclobutyl, cyclopentyl, cyclohexyl, phenyl, 3-dichlorofluoromethyl-phenyl, 3-trifluoromethylphenyl, 3-trichloromethyl-phenyl, 4-methyl-phenyl, 4-chlorophenyl, 4-chloro-3-trifluoromethylphenyl or 4-methyl-3-trifluoromethyl-phenyl radical, or the radical

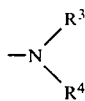

wherein

R³ represents a methyl, ethyl, n-propyl, iso-propyl, n-butyl, iso-butyl, sec.-butyl, allyl, propargyl, cyclopropyl or cyclohexyl radical, and R⁴ represents a methyl, ethyl, n-propyl, iso-propyl, n-butyl, iso-butyl, sec.-butyl, allyl, propargyl, cyclopropyl, cyclohexyl, phenyl, benzyl, phenylethyl, methoxycarbonyl, ethoxycarbonyl, n-propoxycarbonyl, iso-propoxycarbonyl, phenoxycarbonyl, 3-isopropyl-phenoxycarbonyl, 2-isopropoxy-phenoxycarbonyl, 2,3-dihydro-2,2-dimethyl-7-benzofuranyl-oxycarbonyl, allyloxycarbonyl, propargyloxy-carbonyl, methylthiocarbonyl, ethyl-thiocarbonyl, n-propylthiocarbonyl, iso-propyl-thiocarbonyl, n-butylthiocarbonyl, iso-butyl-thiocarbonyl, sec.-butyl-thiocarbonyl, tert.-butyl-thiocarbonyl, phenylthiocarbonyl, methylaminocarbonyl, dimethyl-aminocarbonyl, ethylaminocarbonyl, diethyl-aminocarbonyl, n-propylaminocarbonyl, di-n-propyl-aminocarbonyl, n-butyl-aminocarbonyl, di-n-butyl-aminocarbonyl, di-iso-butyl-aminocarbonyl, aminocarbonyl, chloro-carbonyl, fluoro-carbonyl or bromo-carbonyl radical, a 1-methyl-, 1-ethyl-, 1-n-propyl-, 1-isopropyl-, 1-n-butyl-, 1-iso-butyl-, 1-sec.-butyl-, 1-tert.-butyl-, 1-(2-methybut-2-yl)-, 1-allyl-, 1-propargyl-, 1-cyclopropyl-, 1-cyclobutyl-, 1-cyclopentyl- or 1-cyclohexyl-pyrazol-4-oxy-carbonyl radical or the radical

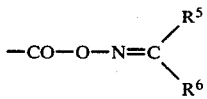

wherein

R⁵ represents a hydrogen atom or a methyl, ethyl, n-propyl, iso-propyl, n-butyl, iso-butyl, sec.-butyl, tert.-butyl, methyl, ethyl-aminocarbonyl, dimethyl-aminocarbonyl or diethyl-aminocarbonyl radical, R⁶ represents a methyl, ethyl, n-propyl, iso-propyl, n-butyl, iso-butyl, sec.-butyl, tert.-butyl, methylthio, ethylthio, n-propylthio, isopropylthio, cyano-methylthio, cyano-ethylthio, methylthiomethyl, methylthio-ethyl, ethylthioethyl, methylsulphonyl-methyl, 1-methylsulphonyleth-1-yl or 2-methylthio-prop-2-yl radical, or R⁵ and R⁶ together represent a norbornen-2-yl and 1,4-dithian-2-yl radical, or wherein R³ and R⁴ together represent a morpholin-4-yl, pyrrolidin-1-yl, piperidin-1-yl, piperazin-1-yl or tetrahydro-4H-1,4-thiazine radical. If, for example, 1-methyl-4-hydroxy-pyrazole and N-ethyl-N-ethylthio-carbamic acid-fluoride are used as starting materials for reaction variant (a), the course of the reaction can be represented by the following equation:

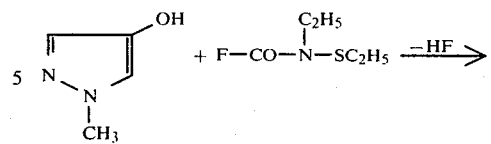

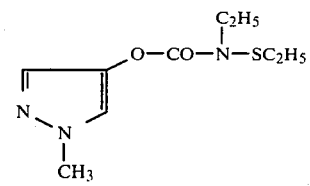

If, for example, 1-methyl-4-hydroxy-pyrazole and di-(fluorocarbonyl-n-propylamino)sulphide are used as starting materials for reaction variant (b), the course of the reaction can be represented by the following equation:

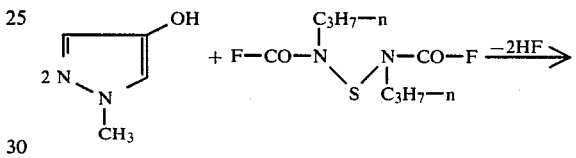

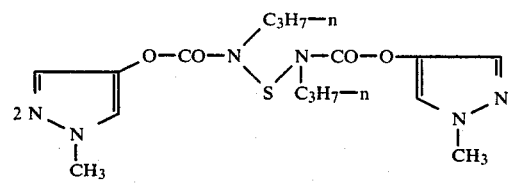

If, for example, trichloromethanesulphenic acid-chloride or sulphur dichloride and N-n-propyl O-(1-methylpyrazol-4-yl) carbamate are used as starting materials for reaction variant (c), the course of the reaction can be represented by the following equations:

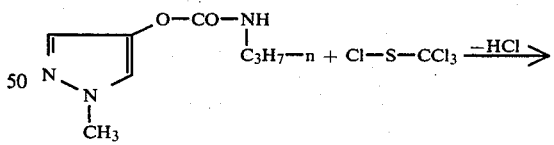

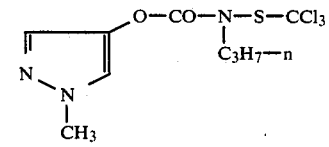

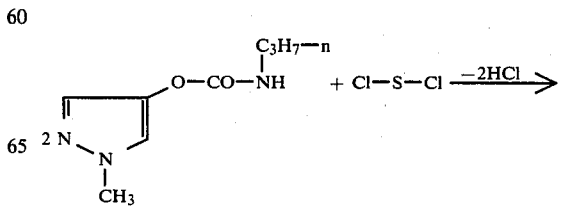

-continued

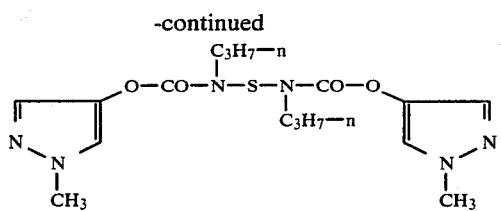

Preferred 4-hydroxy-pyrazoles of formula (II) to be used as starting materials in reaction variants (a) and (b) are those in which R has the same meaning as that given in the definition of preferred and particularly preferred compounds according to the present invention.

The following may be mentioned as examples of the compounds of the formula (II): 1-methyl-, 1-ethyl-, 1-n-propyl-, 1-iso-propyl-, 1-(1,1-dimethylpropyl)-, 1-(2,2-dimethylpropyl)-, 1-n-butyl-, 1-iso-butyl-, 1-sec.-butyl-, 1-tert.-butyl-, 1-(1-methylbutyl)-, 1-(2-methylbutyl)-, 1-(3-methylbutyl)-, 1-n-pentyl-, 2-(1-ethylpropyl)-, 1-cyclopropyl-, 1-cyclobutyl-, 1-cyclopentyl-, 1-cyclohexyl-, 1-allyl-, 1-propargyl-, 1-methylthiomethyl-, 1-(2-cyano-ethyl)-, 1-(2-methoxy-ethyl)-, 1-(2-ethoxyethyl)-, 1-(2-methylthio-ethyl)-, 1-chloromethyl-, 1-dichloromethyl-, 1-trichloromethyl-, 1-(2-chloroethyl)-, and 1-trifluoromethyl-4-hydroxy-pyrazole.

The 4-hydroxypyrazoles of the formula (II) are known (see Liebigs Ann. Chem. 313 (1900), 17 and our DE-OS (German Published Specification) 2,931,033).

The 4-hydroxy-pyrazoles of the formula (II) are obtained, for example, by the reaction of the corresponding 4-methoxypyrazoles with hydrobromic acid. The 4-methoxypyrazoles can be prepared in a known manner, for example by the reaction of appropriate hydrazines with 2-methoxy-4-dimethyl-amino-acrolein (see Archiv der Pharmazie 300, (1967), 704–708).

Preferred N-sulphenylated carbamoyl halides of formula (III) furthermore to be used as starting materials in process variant (a) are those in which $R^1$, $R^2$ and n have the same meanings as those given in the definition of preferred and particularly preferred compounds of the present invention, and X represents a fluorine or chlorine atom.

The following may be mentioned as examples of the compounds of the formula (III):

TABLE 1

$$R^2-S-\underset{R^1}{N}-CO-X \quad (IIIa)$$

| $R^1$ | $R^2$ | $R^1$ | $R^2$ |
|---|---|---|---|
| $C_2H_5$ | $-N(C_4H_9-n)_2$ | $n-C_3H_7$ | $-N(C_4H_9-n)_2$ |
| iso-$C_3H_7$ | $CCl_2F$ | iso-$C_3H_7$ | $-N(C_4H_9-n)_2$ |
| $C_2H_5$ | $CFCl_2$ | $C_2H_5$ | —N(morpholino) |
| $n-C_3H_7$ | $CFCl_2$ | $C_2H_5$ | $C_2H_5$ |
| $CH_2=CH-CH_2$ | $CFCl_2$ | $C_2H_5$ | tert.-$C_4H_9$ |
| cyclopropyl | $CFCl_2$ | $C_2H_5$ | cyclohexyl |
| $CH\equiv C-CH_2$ | $CFCl_2$ | $n-C_3H_7$ | tert.-$C_4H_9$ |
| $n-C_4H_9$ | $CFCl_2$ | cyclohexyl | $CFCl_2$ |
| $C_2H_5$ | $CCl_3$ | cyclohexyl | $CCl_3$ |
| iso-$C_3H_7$ | $CCl_3$ | $n-C_3H_7$ | $CCl_3$ |
| $C_2H_5$ | phenyl | $n-C_3H_7$ | phenyl |
| iso-$C_3H_7$ | phenyl | $CH_2=CH-CH_2-$ | $CCl_3$ |

TABLE 1-continued $$R^2-S-\underset{\underset{R^1}{|}}{N}-CO-X \quad (IIIa)$$

| R¹ | R² | R¹ | R² |
|---|---|---|---|
| C₂H₅ |  (–C₆H₄–CH₃) | 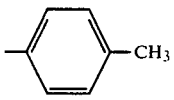 (cyclopropyl) | CCl₃ |
| n-C₃H₇ | 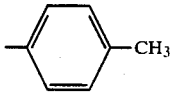 (–C₆H₄–CH₃) | CH≡C–CH₂– | CCl₃ |
| C₂H₅ | 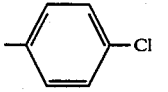 (–C₆H₄–Cl) | n-C₄H₉ | CCl₃ |
| n-C₃H₇ | 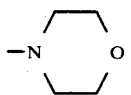 (–C₆H₄–Cl) | n-C₃H₇ | 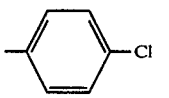 (–N(morpholino)O) |
| C₂H₅ | 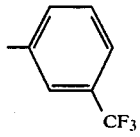 (–C₆H₄–CF₃) | n-C₃H₇ |  (–C₆H₄–CF₃) |
| n-C₃H₇ | 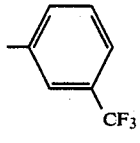 (cyclohexyl) | iso-C₃H₇ | 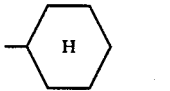 (–C₆H₄–CF₃) |
| n-C₄H₉ | 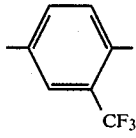 (cyclohexyl) | C₂H₅ | 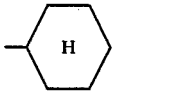 (–C₆H₃(Cl)(CF₃)) |
| C₂H₅ | CH₃ | n-C₄H₉ | 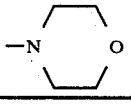 (–N(morpholino)O) |

X = fluorine or chlorine;

N-Sulphenylated carbamoyl halides are known (see DAS (German Published Specification) 1,297,095).

The N-sulphenylated carbamoyl halides of the formula (IIIa) are obtained, for example, by the reaction of the corresponding sulphenyl halides with N-substituted carbamoyl halides in the presence of a diluent (such as toluene, and in the presence of an acid acceptor (such as triethylamine) at a temperature between −10° and 100° C. (see the preparative examples hereinbelow).

Preferred acylating agents of formula (IV) to be used as starting materials in reaction variant (b) are those in which R¹ and n have the same meanings in the definitions of preferred and particularly preferred compounds of formula (I) and X represents a fluorine or chlorine atom.

The following may be mentioned as examples of the compounds of the formula (IV): bis-(N-ethyl-N-fluorocarbonylamino)-, bis-(N-n-propyl-N-fluorocarbonylamino)-, bis-(N-iso-propyl-N-fluorocarbamoylamino)-, bis-(N-2-propen-1-yl-N-fluoro-carbonylamino)-, bis-(N-2-propin-1-yl-N-fluorocarbonylamino)-, bis-(N-cyclopropyl-N-fluorocarbonylamino)-, bis-(N-n-butyl-N-fluorocarbonylamino)-, bis-(N-iso-butyl-N-fluorocarbonylamino)-, bis-(N-n-pentyl-N-fluorocarbonylamino)- and bis-(N-cyclopentyl-N-fluorocarbonylamino)sulphide or disulphide, and the corresponding N-chlorocarbonylamino derivatives.

The acylating agents of the formula (IV) are not known: however, they can be prepared according to known processes (see DAS (German Published Specification) No. 1,297,095). These compounds are obtained, for example, by the reaction of sulphur dichloride or disulphur dichloride with N-substituted carbamoyl halides in the presence of a diluent (such as toluene) and in the presence of an acid acceptor (such as triethylamine)

at a temperature between −30° and 50° C. (see the preparative examples hereinbelow).

Preferred O-pyrazol-4-yl carbamates of formula (V) to be used as starting materials in reaction variant (c) are those in which R and $R^1$ have the same meanings as those given in the definition of preferred and particularly preferred compounds of the present invention.

The following may be mentioned as examples of the compounds of the formula (V): N-n-propyl O-(1-isopropylpyrazol-4-yl)carbamate, N-ethyl O-(1-tert.-butyl-pyrazol-4-yl)carbamate, N-iso-propyl O-(1-isopropyl-pyrazol-4-yl)carbamate, N-ethyl O-(1-isopropyl-pyrazol-4-yl)carbamate, N-n-propyl O-(1-sec.-butyl-pyrazol-4-yl)carbamate, N-ethyl O-(1-(2-methyl-but-2-yl)-pyrazol-4-yl)carbamate, N-n-propyl O-(1-(2-methyl-but-2-yl)-pyrazol-4-yl)carbamte, N-ethyl O-(n-propyl-pyrazol-4-yl)carbamate, N-isopropyl O-(1-(2-methyl-but-2-yl)-pyrazol-4-yl)carbamate, N-ethyl O-(1-ethyl-pyrazol-4-yl)carbamate, N-allyl O-(1-isopropyl-pyrazol-4-yl)carbamate, N-propargyl O-(1-isopropyl-pyrazol-4-yl)carbamate, N-cyclopropyl O-(1-tert.-butyl-pyrazol-4-yl)carbamate, N-cyclopropyl O-(1-(2-methyl-but-2-yl)-pyrazol-4-yl)carbamate, N-allyl O-(1-tert.-butyl-pyrazol-4-yl)carbamate, N-propargyl O-(1-tert.-butyl-pyrazol-4-yl)carbamate, N-cyclopropyl O-(1-isopropyl-pyrazol-4-yl)carbamate, N-allyl O-(1-(2-methyl-but-2-yl)-pyrazol-4-yl carbamate, N-propargyl O-(1-(2-methyl-but-2-yl)-pyrazol-4-yl carbamate, N-allyl O-(1-sec.-butyl-pyrazol-4-yl)carbamate, N-propargyl O-(1-sec.-butyl-pyrazol-4-yl)carbamate, N-cyclopropyl O-(1-sec.-butyl-pyrazol-4-yl)carbamate, N-allyl O-(1-ethyl-pyrazol-4-yl)carbamate, N-propargyl O-(1-ethyl-pyrazol-4-yl)carbamate, N-cyclopropyl O-(1-ethyl-pyrazol-4-yl)carbamate, N-ethyl O-(1-cyclohexyl-pyrazol-4-yl)carbamate, N-ethyl O-(1-sec.-butyl-pyrazol-4-yl)carbamate, N-ethyl O-(1-methyl-pyrazol-4-yl)carbamate, N-ethyl O-(1-cyclopropyl-pyrazol-4-yl)carbamate and N-n-propyl O-(1-tert.-butyl-pyrazol-4-yl)carbamate.

The compounds of the formula (V) form the subject of application Ser. No. 360,138, filed Mar. 22, 1982, now pending.

The compounds of the formula (V) are obtained, for example, by the reaction of 4-hydroxy-pyrazoles of the formula (II) with appropriate isocyanates, in the presence of a diluent (such as acetone, methylene chloride or toluene) and, if appropriate, in the presence of a catalyst (such as triethylamine), at a temperature between 10° and 80° C., or with phosgene and the appropriate amines, in the presence of a diluent (such as toluene) and, if appropriate, in the presence of an acid acceptor (such as triethylamine), at a temperature between −10° and 80° C.

Preferred sulphenyl halides of formula (VI) furthermore to be used as starting materials in reaction variant (c) are those in which $R^7$ represents a halogen atom, or has the same meaning as that given for $R^2$ in the definition of preferred and particularly preferred compounds of the present invention, n is 1 or 2 and Y represents a fluorine or chlorine atom.

The following may be mentioned as examples of the compounds of the formula (VI): sulphur dichloride and disulphur dichloride, and methane-, ethane-, n-propane-, n-butane-, iso-butane-, sec.-butane-, tert.-butane-, 2-methyl-but-2-ane-, 2,2-dimethyl-prop-2-ane-, tri-chloromethane-, dichlorofluoromethane-, chlorodifluoromethane-, allyl-, propargyl-, cyclopropane- and cyclohexanesulphenic acid-chloride; thiophenyl chloride, and 3-dichlorofluoromethyl-, 3-trifluoromethyl-, 3-trichloromethyl-, 4-methyl-, 4-chloro-, 4-chloro-3-trifluoromethyl- and 4-methyl-3-trifluoromethyl-thiophenyl chloride; dimethyl-, diethyl-, di-n-propyl- and di-n-butyl-aminosulphenic acid-chloride; and 4-morpholino-, pyrrolidino-, piperidino- and tetrahydro-4H-1,4-thiazino-sulphenic acid-chloride.

Compounds which can be carbamoylated and which may be employed as starting materials in reaction variant (b) are preferably:

(i) an aliphatic or alicyclic, saturated or unsaturated alcohol, mercaptan or amine, each of which contains up to 6 carbon atoms in the alkyl radical, (ii) a phenol, thiophenol or hydroxy-pyrazole, each of which is optionally substituted by halogen and/or by optionally halogen-substituted radical(s) selected from alkyl, alkoxy, alkenyl and alkinyl having up to 6 carbon atoms, and cycloalkyl having up to 7 carbon atoms; and (iii) a hydroxylamine derivative of the general formula

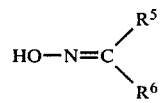

in which $R^5$ represents a hydrogen atom, an alkyl radical or a mono- or dialkylaminocarbonyl radical, and $R^6$ represents an alkyl, alkylthio, cyano-alkylthio, alkylsulphonyl-alkyl or alkylthio-alkyl radical, or $R^5$ and $R^6$ together represent an alkanediyl radical which is optionally interrupted by oxygen, sulphur or a sulphinyl or sulphonyl grouping.

The following may be mentioned as examples of the compounds which can be carbamoylated: methanol, ethanol, n-propanol, isopropanol, allyl alcohol, propargyl alcohol, 3,3-dimethyl-allyl alcohol, cyclohexanol, ethylmercaptan, propylmercaptan, isopropylmercaptan, dimethylamine, isopropylamine, morpholine, 3-methyl-but-2-ene-1-ol, phenol, thiophenol, 3-isopropyl-phenol, 2-isopropoxyphenol, 2,3-dihydro-2,2-dimethyl-7-hydroxy-benzofuran, di-n-butylamine, n-butanol, iso-butanol, tert.-butanol, 4-chlorophenol, 1-methylthio-acetaldehyde-oxime, 2-methylthioisobutyraldoxime, 2-methyl-2-methylthio-propanaldoxime, 1-methyl-thio-1-dimethylamino-carbonyl-methanaldoxime and 3,3-dimethyl-1-methylthio-butan-2-one-oxime, and the compounds listed above as examples of 4-hydroxypyrazoles of the formula (II).

The reaction variants (a), (b) and (c) according to the invention are preferably carried out using a diluent. Virtually any of the inert organic solvents are suitable diluents. These include, in particular, aliphatic and aromatic, optionally halogenated hydrocarbons (such as pentane, hexane, heptane, cyclohexane, petroleum ether, petrol, ligroin, benzene, toluene, xylene, methylene chloride, ethylene chloride, chloroform, carbon tetrachloride, chlorobenzene and o-dichlorobenzene), ethers (such as diethyl ether and dibutyl ether, glycol dimethyl ether and diglycol dimethyl ether, tetrahydrofuran and dioxane), ketones (such as acetone, methyl ethyl ketone, methyl isopropyl ketone and methyl isobutyl ketone), esters (such as methyl acetate and ethyl acetate), nitriles (such as acetonitrile and propionitrile), amides (such as dimethylformamide, dimethylacetamide and N-methylpyrrolidone), dimethylsulphoxide, tetramethylenesulphone and hexamethylphosphoric acid triamide. Toluene is preferably used as the diluent.

Any of the customary acid-binding agents can be used as acid acceptors. Alkali metal carbonates and alcoholates (such as sodium carbonate and potassium carbonate, and sodium and potassium methylate or ethylate) and also aliphatic, aromatic or heterocyclic amines (for example triethylamine, trimethylamine, dimethylaniline, dimethylbenzylamine, pyridine and diazabicycloundecene) have proved particularly suitable. Triethylamine is preferably employed as the acid acceptor.

The reaction temperature can be varied within a relatively wide range. In general, the reaction is carried out at a temperature between −20° and 100° C., preferably between 0° and 80° C.

The processes according to the invention are carried out in general under normal pressure.

To carry out the processes according to the invention, the starting materials are customarily employed in equivalent amounts. An excess of one or the other of the reaction components brings no substantial advantages. The reaction is carried out in general in a suitable diluent, in the presence of an acid acceptor, and the reaction mixture is stirred for several hours at the required temperature. Thereafter, a water-immiscible organic solvent, for example toluene, is added, if appropriate, and the organic phase is worked up in the customary manner by washing it and drying it and distilling off the solvent. The products are obtained in this manner in an oily or crystalline form. They are characterized by their melting point or refractive index.

Some of the new compounds are obtained in the form of oils, which in some cases cannot be distilled without decomposition, but are freed from the last volatile constituents by so-called "incipient distillation", that is to say by prolonged heating to moderately elevated temperatures under reduced pressure, and are purified in this manner. They are characterized by their refractive index.

The N-substituted O-pyrazol-4-yl carbamates according to the present invention not only exhibit an insecticidal and nematicidal action, but also have a good fungicidal in vitro action.

The active compounds are well tolerated by plants, have a favorable level of toxicity to warm-blooded animals, and are suitable for combating arthropod pests, especially insects, arachnida and nematodes, which are encountered in agriculture, in forestry, in the protection of stored products and of materials, and in the hygiene field. They are active against normally sensitive and resistance species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisseliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro*, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meliodogyne spp., Aphelenchoides spp., Longidorus spp., Xiphinema spp., and Trichodorus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as a good stability to alkali on limed substrates.

The present invention also provides pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular insects, acarids or nematodes) which comprises applying to the pests, or to a habitat thereof, a compound of the present invention alone or in the form of a composition containing as active ingredient a compound of the present invention in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATION OF STARTING MATERIALS

The N-sulphenylated carbamoyl halides of the formula (III) which are to be used as starting materials can be prepared, for example, as follows:

Example 1

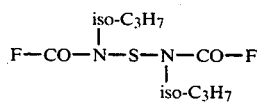

20.6 g (0.2 mol) of sulphur dichloride are added to a solution of 42 g (0.4 mol) of N-isopropylcarbamoyl fluoride in 200 ml of toluene at room temperature. Thereafter, 40.4 g (0.4 mol) of triethylamine are added dropwise at $-10°$ to $-20°$ C., and the mixture is stirred for a further 24 hours, without cooling. The mixture is then extracted by shaking it with twice 50 ml of water. The organic phase is dried over sodium sulphate and is then evaporated down in vacuo. By distilling the residue, 15 g (31% of theory) of bis-(N-isopropyl-N-fluorocarbonylamino)sulphide are obtained in the form of a yellow oil of boiling point 65° C./0.2 mm Hg.

The following compounds of the formula

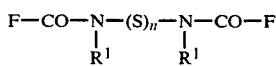  (IV)

are obtained in an analogous manner

TABLE 2

| n | $R^1$ | Yield (% of theory) | Boiling point (°C./mm Hg) |
|---|---|---|---|
| 1 | $C_2H_5$ | 63 | 105/10 |
| 1 | $n-C_3H_7$ | 52 | 70/0.01 |

Example 2

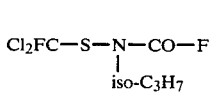

50.5 g (0.5 mol) of triethylamine are added dropwise to a mixture of 84.8 g (0.5 mol) of dichlorofluoromethanesulphenyl chloride, 52.5 g (0.5 mol) of N-isopropylcarbamoyl fluoride and 500 ml of toluene at 0°–5° C. Thereafter, the mixture is stirred for a further 24 hours at 40° C. and is extracted by shaking it with twice 100 ml of ice-water, and the organic phase is then dried over sodium sulphate. After the solvent has been stripped off, the residue is distilled in vacuo. 25 g (21% of theory) of N-isopropyl-N-fluorodichloromethylthiocarbamoyl fluoride of boiling point 78°–79° C./10 mm Hg are obtained in this manner.

The following compounds of the formula

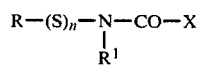  (III)

are obtained in an analogous manner

TABLE 3

| n | X | R | $R^1$ | Yield (% of theory) | Boiling point (°C./mm Hg); Refractive index |
|---|---|---|---|---|---|
| 1 | F | $C_2H_5$ | $CFCl_2$ | 49 | 68–69/10 |
| 1 | F | $n-C_3H_7$ | $CFCl_2$ | 44 | 78–80/10 |
| 1 | F(Cl) | $CH_2=CH-CH_2$ | $CFCl_2$ | | |
| 1 | F(Cl) | △ | $CFCl_2$ | | |
| 1 | F(Cl) | $CH\equiv C-CH_2$ | $CFCl_2$ | | |
| 1 | F(Cl) | $n-C_4H_9$ | $CFCl_2$ | | |
| 1 | F(Cl) | $C_2H_5$ | $CCl_3$ | | |
| 1 | F(Cl) | iso-$C_3H_7$ | $CCl_3$ | | |
| 1 | F | $C_2H_5$ | ⌬ | 63 | 70–71/0.01 |
| 1 | F | $n-C_3H_7$ | ⌬ | 54 | 88–90/0.01 |
| 1 | F | iso-$C_3H_7$ | ⌬ | 26 | 96–98/0.01 |
| 1 | F(Cl) | $C_2H_5$ | ⌬–$CH_3$ | | |

TABLE 3-continued

| n | X | R | R¹ | Yield (% of theory) | Boiling point (°C./mm Hg); Refractive index |
|---|---|---|---|---|---|
| 1 | F(Cl) | n-$C_3H_7$ | —C₆H₄—CH₃ (para) | | |
| 1 | F(Cl) | $C_2H_5$ | —C₆H₄—Cl (para) | | |
| 1 | F(Cl) | n-$C_3H_7$ | —C₆H₄—Cl (para) | | |
| 1 | F(Cl) | $C_2H_5$ | —C₆H₄—$CF_3$ (meta) | | |
| 1 | F(Cl) | n-$C_3H_7$ | —C₆H₄—$CF_3$ (meta) | | |
| 1 | F(Cl) | iso-$C_3H_7$ | —C₆H₄—$CF_3$ (meta) | | |
| 1 | F(Cl) | $C_2H_5$ | —C₆H₃(Cl)($CF_3$) | | |
| 1 | F(Cl) | $C_2H_5$ | $CH_3$ | | |
| 1 | F(Cl) | $C_2H_5$ | —N(n-$C_4H_9$)$_2$ | | |
| 1 | F(Cl) | n-$C_3H_7$ | —N(n-$C_4H_9$)$_2$ | | |
| 1 | F(Cl) | iso-$C_3H_7$ | —N(n-$C_4H_9$)$_2$ | | |
| 1 | F(Cl) | $C_2H_5$ | —N(morpholino) | | |
| 1 | F(Cl) | $C_2H_5$ | $C_2H_5$ | | |
| 1 | F(Cl) | $C_2H_5$ | tert.-$C_4H_9$ | | |
| 1 | F(Cl) | $C_2H_5$ | —C₆H₁₁ | | |
| 1 | F(Cl) | n-$C_3H_7$ | tert.-$C_4H_9$ | | |

PREPARATIVE EXAMPLES

Example 3

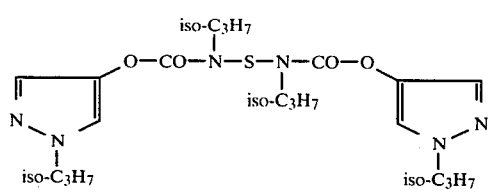

(Reaction variant (b))

5 g (0.05 mol) of triethylamine are added dropwise to a mixture of 6.3 g (0.05 mol) of 1-isopropyl-4-hydroxypyrazole, 80 ml of toluene and 6 g (0.025 mol) of bis(N-isopropyl-N-fluorocarbonyl-amino)sulphide (Example 1) at 20°–25° C., and the mixture is then stirred for a further 10 hours at room temperature. Thereafter, the mixture is extracted by shaking with twice 25 ml of water, the organic phase is dried over sodium sulphate, and the solvent is distilled off in vacuo. 6 g (53% of theory) of bis[N-isopropyl-N-(1-isopropyl-pyrazol-4-yloxy)carbonylamino]sulphide remain in the form of a beige powder of melting point 88° C.

Example 4

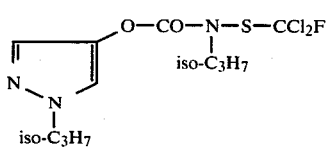

(Reaction variant (a))

5 g (0.05 mol) of triethylamine are added to a solution of 6.3 g (0.05 mol) of 1-isopropyl-4-hydroxypyrazole and 11.9 g (0.05 mol) of N-isopropyl-N-fluorodichloromethylthiocarbamoyl fluoride (Example 2) in 80 ml of toluene at room temperature. The mixture is stirred for a further 12 hours at room temperature and is shaken with twice 25 ml of water, the organic phase is dried over sodium sulphate, and the solvent is then distilled off. The residue is subjected to incipient distillation in a high vacuum. 13 g (76% of theory) of N-isopropyl N-fluorodichloromethylthio O-(1-isopropyl-pyrazol-4-yl)carbamate are thus obtained in the form of a brown oil of refractive index $n_D^{20}$: 1.5072.

Example 5

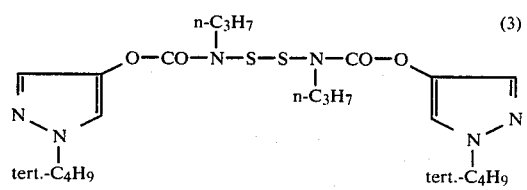

(Reaction variant (c))

3.5 g (0.025 mol) of disulphur dichloride are added dropwise to a mixture of 11.2 g (0.05 mol) of N-n-propyl O-(1-tert.-butyl-pyrazol-4-yl)carbamate, 5 g (0.055 mol) of triethylamine and 200 ml of toluene at 0°–5° C. The mixture is stirred for a further 18 hours at room temperature and is then washed with twice 100 ml of water. The organic phase is dried over sodium sulphate, and the solvent is then distilled off in vacuo. 8 g (31% of theory) of bis-[N-n-propyl-N-(1-tert.-butylpyrazol-4-yloxy)-carbonylamino]disulphide remain in the form of a beige powder of melting point 61° C.

The following compounds of the formula

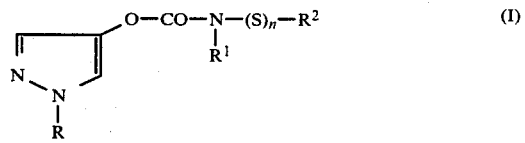

can be prepared analogously to one of the Examples 3, 4 or 5:

TABLE 4

| Compound No. | n | R | $R^1$ | $R^2$ | Yield (% of theory) | Refractive index; melting point (°C.) |
|---|---|---|---|---|---|---|
| 4 | 1 | tert.-C4H9 | iso-C3H7 | iso-C3H7—N—CO—O—⟨pyrazole⟩—N—tert.-C4H9 | 67 | $n_D^{20}$: 1.4985 |
| 5 | 1 | tert.-C4H9 | iso-C3H7 | —CCl2F | 84 | $n_D^{20}$: 1.5039 |
| 6 | 1 | iso-C3H7 | C2H5 | C2H5—N—CO—O—⟨pyrazole⟩—N—iso-C3H7 | 94 | $n_D^{21}$: 1.5134 |
| 7 | 1 | tert.-C4H9 | C2H5 | C2H5—N—CO—O—⟨pyrazole⟩—N—tert.-C4H9 | 84 | $n_D^{21}$: 1.5112 |
| 8 | 1 | iso-C3H7 | C2H5 | —CCl2F | 85 | $n_D^{21}$: 1.5050 |
| 9 | 1 | tert.-C4H9 | C2H5 | —CCl2F | 87 | $n_D^{21}$: 1.5041 |
| 10 | 1 | iso-C3H7 | n-C3H7 | —CCl2F | 81 | $n_D^{21}$: 1.5012 |
| 11 | 1 | tert.-C4H9 | n-C3H7 | —CCl2F | 84 | $n_D^{22}$: 1.5073 |

TABLE 4-continued

| Compound No. | n | R | R¹ | R² | Yield (% of theory) | Refractive index; melting point (°C.) |
|---|---|---|---|---|---|---|
| 12 | 1 | iso-$C_3H_7$ | n-$C_3H_7$ | n-$C_3H_7$—N(—)—CO—O—[pyrazole]—N—iso-$C_3H_7$ | 80 | $n_D^{22}$: 1.5022 |
| 13 | 1 | tert.-$C_4H_9$ | n-$C_3H_7$ | n-$C_3H_7$—NCO—O—[pyrazole]—N—tert.-$C_4H_9$ | 98 | $n_D^{24}$: 1.5039 |
| 14 | 1 | iso-$C_3H_7$ | $C_2H_5$ | $C_2H_5$—N—CO—O—N=C($CH_3$)($SCH_3$) | 89 | $n_D^{24}$: 1.5294 |
| 15 | 1 | tert.-$C_4H_9$ | $C_2H_5$ | $C_2H_5$—N—CO—O—N=C($CH_3$)($SCH_3$) | 96 | $n_D^{24}$: 1.5268 |
| 16 | 1 | $CH_3$ | $C_2H_5$ | $C_2H_5$—N—CO—O—[pyrazole]—N—$CH_3$ | | |
| 17 | 1 | $C_2H_5$ | $C_2H_5$ | $C_2H_5$—N—CO—O—[pyrazole]—N—$C_2H_5$ | | |
| 18 | 1 | n-$C_3H_7$ | $C_2H_5$ | $C_2H_5$—N—CO—O—[pyrazole]—N—n-$C_3H_7$ | | |
| 19 | 1 | $CH_3$—$CH_2$—C($CH_3$)($CH_3$)— | $C_2H_5$ | $C_2H_5$—N—CO—O—[pyrazole]—N—C($CH_3$)($CH_3$)($CH_2CH_3$) | | |
| 20 | 1 | $CH_3$—$CH_2$—C($CH_3$)($CH_3$)— | $C_2H_5$ | —$CCl_2F$ | | |
| 21 | 1 | cyclopropyl | $C_2H_5$ | $C_2H_5$—N—CO—O—[pyrazole]—N—cyclopropyl | | |
| 22 | 1 | cyclopropyl | $C_2H_5$ | —$CCl_2F$ | | |
| 23 | 1 | cyclohexyl | $C_2H_5$ | $C_2H_5$—N—CO—O—[pyrazole]—N—cyclohexyl | | |
| 24 | 1 | cyclohexyl | $C_2H_5$ | —$CCl_2F$ | | |

TABLE 4-continued
| Compound No. | n | R | R¹ | R² | Yield (% of theory) | Refractive index; melting point (°C.) |
|---|---|---|---|---|---|---|
| 25 | 1 | tert.-C₄H₉ | CH₂=CH—CH₂ | 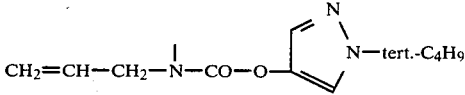 | | |
| 26 | 1 | tert.-C₄H₉ | CH≡C—CH₂ | 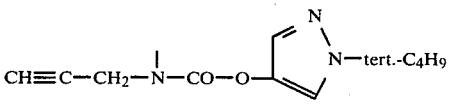 | | |
| 27 | 1 | tert.-C₄H₉ |  | 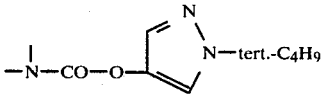 | | |
| 28 | 1 | tert.-C₄H₉ | CH₂=CH—CH₂ | —CCl₂F | | |
| 29 | 1 | tert.-C₄H₉ | CH≡C—CH₂ | —CCl₂F | | |
| 30 | 1 | tert.-C₄H₉ |  | —CCl₂F | | |
| 31 | 1 | iso-C₃H₇ | C₂H₅ | 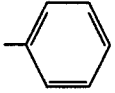 | | |
| 32 | 1 | iso-C₃H₇ | n-C₃H₇ | 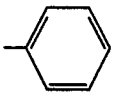 | | |
| 33 | 1 | tert.-C₄H₉ | C₂H₅ | 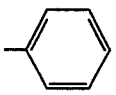 | 98 | $n_D^{18}$: 1.5461 |
| 34 | 1 | tert.-C₄H₉ | n-C₃H₇ | 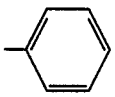 | 98 | $n_D^{18}$: 1.5465 |
| 35 | 1 | tert.-C₄H₉ | C₂H₅ | 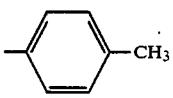 | | |
| 36 | 1 | tert.-C₄H₉ | n-C₃H₇ | 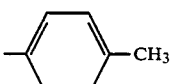 | | |
| 37 | 1 | tert.-C₄H₉ | C₂H₅ | 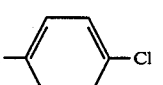 | | |
| 38 | 1 | iso-C₃H₇ | C₂H₅ | 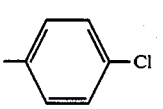 | | |

TABLE 4-continued

| Compound No. | n | R | R¹ | R² | Yield (% of theory) | Refractive index; melting point (°C.) |
|---|---|---|---|---|---|---|
| 39 | 1 | sec.-$C_4H_9$ | $C_2H_5$ | —C$_6$H$_4$-CF$_3$ | | |
| 40 | 1 | iso-$C_3H_7$ | $C_2H_5$ | —C$_6$H$_4$-CF$_3$ | | |
| 41 | 1 | tert.-$C_4H_9$ | $C_2H_5$ | —C$_6$H$_4$-CF$_3$ | | |
| 42 | 1 | $CH_3-CH_2-C(CH_3)_2-$ | $C_2H_5$ | —C$_6$H$_4$-CF$_3$ | | |
| 43 | 1 | cyclohexyl (H) | $C_2H_5$ | —C$_6$H$_4$-CF$_3$ | | |
| 44 | 1 | tert.-$C_4H_9$ | n-$C_3H_7$ | —C$_6$H$_4$-CF$_3$ | | |
| 45 | 1 | tert.-$C_4H_9$ | iso-$C_3H_7$ | —C$_6$H$_4$-CF$_3$ | | |
| 46 | 1 | tert.-$C_4H_9$ | $C_2H_5$ | —C$_6$H$_3$(Cl)(CF$_3$) | | |
| 47 | 1 | iso-$C_3H_7$ | $C_2H_5$ | $CH_3$ | | |
| 48 | 1 | tert.-$C_4H_9$ | $C_2H_5$ | $CH_3$ | | |
| 49 | 1 | tert.-$C_4H_9$ | $C_2H_5$ | —N(n-$C_4H_9$)$_2$ | | |
| 50 | 1 | tert.-$C_4H_9$ | iso-$C_3H_7$ | —N(n-$C_4H_9$)$_2$ | | |
| 51 | 1 | tert.-$C_4H_9$ | n-$C_3H_7$ | —N(n-$C_4H_9$)$_2$ | | |
| 52 | 1 | tert.-$C_4H_9$ | $C_2H_5$ | —N(morpholino)O | | |
| 53 | 1 | iso-$C_3H_7$ | $C_2H_5$ | $C_2H_5$ | | |
| 54 | 1 | iso-$C_3H_7$ | $C_2H_5$ | tert.-$C_4H_9$ | | |

TABLE 4-continued

| Compound No. | n | R | R¹ | R² | Yield (% of theory) | Refractive index; melting point (°C.) |
|---|---|---|---|---|---|---|
| 55 | 1 | iso-$C_3H_7$ | $C_2H_5$ | —⟨cyclohexyl-H⟩ | | |
| 56 | 1 | tert.-$C_4H_9$ | $C_2H_5$ | tert.-$C_4H_9$ | | |
| 57 | 1 | tert.-$C_4H_9$ | $C_2H_5$ | $C_2H_5$ | | |
| 58 | 1 | tert.-$C_4H_9$ | $C_2H_5$ | —⟨cyclohexyl-H⟩ | | |
| 59 | 1 | tert.-$C_4H_9$ | n-$C_3H_7$ | tert.-$C_4H_9$ | | |
| 60 | 1 | ⟨cyclohexyl-H⟩ | $C_2H_5$ | —⟨cyclohexyl-H⟩ | | |
| 61 | 1 | tert.-$C_4H_9$ | $C_2H_5$ | —$CCl_3$ | | |
| 62 | 1 | iso-$C_3H_7$ | $C_2H_5$ | —$C_2H_5$—N(—CO—O—iso-$C_3H_7$)— | | |
| 63 | 1 | iso-$C_3H_7$ | $C_2H_5$ | —$C_2H_5$—N(—CO—O—phenyl)— | | |
| 64 | 1 | tert.-$C_4H_9$ | $C_2H_5$ | $C_2H_5$—N(—CO—S—phenyl)— | | |
| 65 | 1 | tert.-$C_4H_9$ | $C_2H_5$ | $C_2H_5$—N(—CO—NH—iso-$C_3H_7$)— | | |
| 66 | 1 | tert.-$C_4H_9$ | $C_2H_5$ | $C_2H_5$—N(—CO—S$C_2H_5$)— | | |
| 67 | 2 | tert.-$C_4H_9$ | $CH_2$—CH=$CH_2$ | $CH_2$=CH—$CH_2$—N(—CO—O—pyrazolyl-N—tert.-$C_4H_9$)— | | |
| 68 | 2 | tert.-$C_4H_9$ | $C_2H_5$ | $C_2H_5$—N(—CO—O—pyrazolyl-N—tert.-$C_4H_9$)— | | |
| 69 | 2 | $CH_3$—$CH_2$—C($CH_3$)($CH_3$)— | $C_2H_5$ | $C_2H_5$—N(—CO—O—pyrazolyl-N—C($CH_3$)($CH_3$)—$CH_2$—$CH_3$)— | | |
| 70 | 1 | tert.-$C_4H_9$ | iso-$C_3H_7$ | —⟨phenyl⟩ | 84 | $n_D^{18}$: 1.5533 |

The pesticidal activity of the compounds of this invention is illustrated by the following biotest examples.

In these examples, the compounds according to the present invention are each identified by the number (given in brackets) from Examples 3, 4 and 5 and Table 4.

The known comparison compounds are identified as follows:

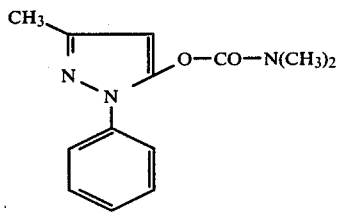
(A)

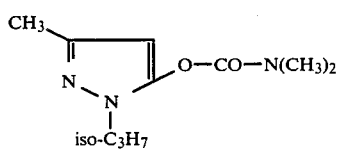
(B)

Example 6

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27 degrees C.

After 4 months, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

In this test, for example, the following compounds showed a superior activity compared to the prior art: (1), (4), (5), (6), (7), (9), (11), (12), (13) and (15).

Example 7

Root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead animals. The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (1), (4), (14) and (15).

Example 8

Root-systemic action
Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil was decisive.

The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (1), (2), (4), (5), (6), (7), (8), (9), (10), (11), (12), (13), (14) and (15).

Example 9

Test insects: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil. The treated soil was filled into pots and the pots were left to stand at room temperature.

After 24 hours the test insects were introduced into the treated soil and after a further 7 days the degree of effectiveness of the active compound was determined in % by counting the dead and the live test insects. The degree of effectiveness was 100% of all of the test insects had been killed and was 0% if exactly as many test insects were still alive as in the case of the untreated control.

In this test, for example, the following compound showed a superior action compared to the prior art: (2).

Example 10

Test insects: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil. The treated soil was filled into pots and the pots were left to stand at room temperature.

After 24 hours the test insects were introduced into the treated soil and after a further 2 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared to the prior art: (2), (4), (5), (7), (9) and (15).

Example 11

*Phaedon Larvae* test
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) were treated by being dipped into the preparation of the active compound of the desired concentration and were infested with mustard beetle larvae (*Phaedon cochleariae*), as long as the leaves were still wet.

After the specified periods of time, the destruction in % was determined. 100% meant that all the beetle larvae had been killed; 0% meant that none of the beetle larvae had been killed.

In this test, for example, the following compounds showed a superior activity compared to the prior art: (1), (2), (4), (5), (6), (7), (8), (9), (10), (11), (12), (13), (14) and (15).

Example 12

Tetranychus test (resistant)
Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Phaseolus vulgaris*) which were heavily infested with the common spider mite or two-spotted spider mite (*Tetranychus urticae*) in all stages of development were treated by being dipped into the preparation of the active compound of the desired concentration.

After the specified periods of time, the destruction in % was determined. 100% meant that all the spider mites had been killed; 0% meant that none of the spider mites had been killed.

In this test, for example, the following compounds showed a superior activity compared to the prior art: (2), (4), (5), (8), (9), (10) and (11).

It is understood that the specification and examples are illustrative but not limitative of the present invention and that other embodiments within the spirit and scope of the invention will suggest themselves to those skilled in the art.

We claim:

1. A compound of the formula

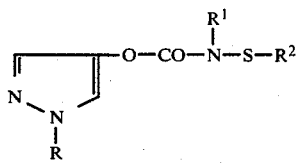

in which

R is a straight-chain or branched alkyl radical which has 1 to 6 carbon atoms;
$R^1$ is a straight-chain or branched alkyl radical having 2 to 6 carbon atoms;
$R^2$ is an alkyl radical which has 1 to 6 carbon atoms and is optionally substituted by up to 3 halogen atoms; or represents the radical

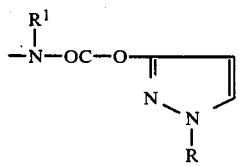

2. A compound according to claim 1 in which

R is a methyl, ethyl, n-propyl, iso-propyl, n-butyl, iso-butyl, sec.-butyl, tert.-butyl, 2-methylbut-2-yl or 2,2-dimethylprop-1-yl radical, $R^1$ is an ethyl, n-propyl, iso-propyl, n-butyl, iso-butyl, sec.-butyl or tert.-butyl radical, $R^2$ is a methyl, ethyl, n-propyl, iso-propyl, n-butyl, iso-butyl, sec.-butyl, tert.-butyl, 2-methylbut-2-yl, 2,2-dimethylprop-1-yl, trichloro-methyl, dichlorofluoromethyl, chloro-difluoromethyl, trifluoromethyl, or the radical

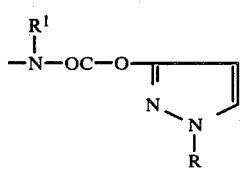

3. A compound according to claim 1, wherein such compound is

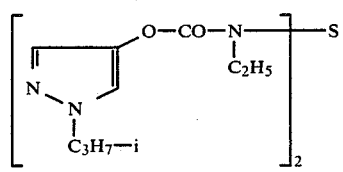

4. A compound according to claim 1, wherein such compound is

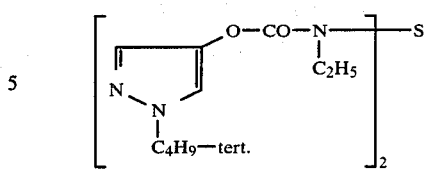

5. A compound according to claim 1, wherein such compound is

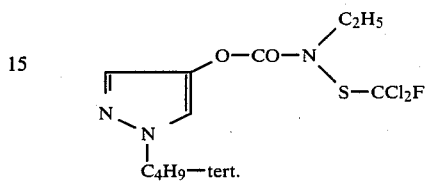

6. An insecticidal composition comprising an insecticidally effective amount of a compound according to claim 1 and a carrier or diluent.

7. A method of combating insects which comprises applying to the insects or to a habitat thereof an insecticidally effective amount of a compound according to claim 1.

* * * * *